United States Patent [19]

Cantatore et al.

[11] Patent Number: 4,999,392
[45] Date of Patent: Mar. 12, 1991

[54] NOVEL PIPERIDINE COMPOUNDS

[75] Inventors: Giuseppe Cantatore, Bitonto; Valerio Borzatta, Bologna, both of Italy

[73] Assignee: Ciba-Geigy Corproation, Ardsley, N.Y.

[21] Appl. No.: 224,028

[22] Filed: Jul. 21, 1988

Related U.S. Application Data

[62] Division of Ser. No. 854,742, Apr. 22, 1986, Pat. No. 4,780,493.

[30] Foreign Application Priority Data

Apr. 22, 1985 [IT] Italy ................. 20441 A/85

[51] Int. Cl.$^5$ ................. C08K 5/3935; C07D 211/00
[52] U.S. Cl. ................. 524/99; 529/102; 529/103; 546/186; 546/187; 546/188; 546/189; 596/190; 252/403
[58] Field of Search ................. 524/99, 102, 103; 546/186, 187, 188, 189, 190; 252/403

[56] References Cited

U.S. PATENT DOCUMENTS

| | | | |
|---|---|---|---|
| 3,543,306 | 11/1970 | Biland | 546/190 |
| 3,982,006 | 3/1976 | Hall | 424/267 |
| 4,094,028 | 6/1978 | Hall et al. | 546/190 |
| 4,191,683 | 3/1980 | Brunetti et al. | 524/590 |
| 4,525,503 | 6/1985 | Cantatore | 524/98 |
| 4,670,488 | 6/1987 | Maegawa et al. | 524/98 |
| 4,736,017 | 3/1988 | Avar | 524/103 |
| 4,751,281 | 8/1988 | Cantatore et al. | 528/289 |

*Primary Examiner*—Kriellion Morgan
*Attorney, Agent, or Firm*—Harry Falber

[57] ABSTRACT

Novel piperidine compounds of the general formula (I)

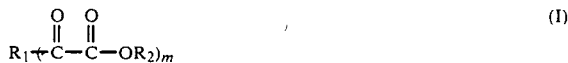

in which m is an integer from 1 to 4, $R_1$ and $R_2$ are as defined in claim 1 and at least one 2,2,6,6-tetramethylpiperidinyl group, being present in $R_1$ or $R_2$ are useful as light stabilizers, heat stabilizers and oxidation stabilizers for organic material, especially for synthetic polymers.

6 Claims, No Drawings

NOVEL PIPERIDINE COMPOUNDS

This is a divisional of application Ser. No. 854,742 filed on Apr. 22, 1986, now U.S. Pat. No. 4,780,493.

The present invention relates to novel piperidine compounds and their use as light stabilisers, heat stabilisers and oxidation stabilisers for organic material, especially for synthetic polymers.

In order to delay the negative effect of ultraviolet radiation on polymers, it has been proposed to use various stabilisers which protect against light; in particular, U.S. Pat. No. 4,525,503 describes piperidine esters of carbamic acids.

The present invention is concerned with novel oxamates of the general formula (I)

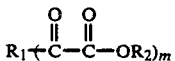  (I)

in which m is an integer from 1 to 4 and, if m=1, $R_1$ is a group

in which $R_3$ and $R_4$ are identical or different and are hydrogen, $C_1$–$C_{18}$-alkyl, $C_2$–$C_6$-alkyl substituted by a $C_1$–$C_{18}$-alkoxy or by a $C_2$–$C_{18}$-dialkylamino, $C_5$–$C_{18}$-cycloalkyl, $C_3$–$C_{18}$-alkenyl, $C_6$–$C_{18}$-aryl unsubstituted or substituted by $C_1$–$C_{12}$-alkoxy, by $C_1$–$C_{12}$-alkyl and/or by —OH, $C_7$–$C_{18}$-aralkyl unsubstituted or substituted by $C_1$–$C_{12}$-alkyl and/or by —OH or are a group of the formula (II)

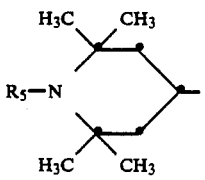  (II)

where $R_5$ is hydrogen, 0., cyanomethyl, $C_1$–$C_{12}$-alkyl, $C_3$–$C_{12}$-alkenyl, $C_3$–$C_{12}$-alkynyl, $C_7$–$C_{12}$-aralkyl unsubstituted or substituted by $C_1$–$C_{12}$-alkyl, or is $C_1$–$C_{12}$-acyl, or $R_1$ is a 5-membered to 13-membered heterocyclic group containing at least one nitrogen atom being linked to the —COCOOR$_2$ radical, or if m=2, $R_1$ is a group

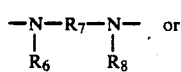

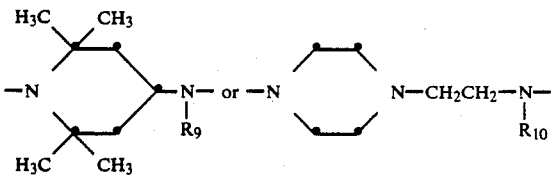

in which $R_6$, $R_8$, $R_9$ and $R_{10}$ are identical or different and are hydrogen, $C_1$–$C_{18}$-alkyl, $C_5$–$C_{18}$-cycloalkyl unsubstituted or substituted by $C_1$–$C_{12}$-alkyl, $C_3$–$C_{18}$-alkenyl, $C_6$–$C_{18}$-aryl unsubstituted or substituted by $C_1$–$C_{12}$-alkoxy, by $C_1$–$C_{12}$-alkyl and/or by —OH, $C_7$–$C_{18}$-aralkyl unsubstituted or substituted by $C_1$–$C_{12}$-alkyl and/or by —OH, or are a group of the formula (II) and $R_7$ ist $C_2$–$C_{18}$-alkylene, $C_6$–$C_{18}$-cycloalkylene, $C_6$–$C_{18}$-arylene, $C_7$–$C_{18}$-aralkylene or a group —$R_{11}$—X—($R_{12}$—X)$_n$—$R_{11}$—, where $R_{11}$ and $R_{12}$ are identical or different and are $C_2$–$C_6$-alkylene and X is —O— or

$R_{13}$ being hydrogen, $C_1$–$C_{12}$-alkyl, $C_5$–$C_{12}$-cycloalkyl unsubstituted or substituted by $C_1$–$C_{12}$-alkyl, or a group of the formula (II) and n is zero, 1 or 2, or $R_1$ is a 5-membered to 7-membered divalent heterocyclic group containing 2 nitrogen atoms being linked to the —COCOOR$_2$ radicals, or if m=3, $R_1$ is a group

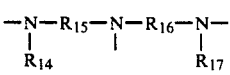

in which $R_{14}$ and $R_{17}$ are identical or different and are hydrogen, $C_1$–$C_{18}$-alkyl, $C_5$–$C_{12}$-cycloalkyl unsubstituted or substituted by $C_1$–$C_{12}$-alkyl, $C_7$–$C_{18}$-aralkyl unsubstituted or substituted by $C_1$–$C_{12}$-alkyl and/or by —OH, or are a group of the formula (II) and $R_{15}$ and $R_{16}$ are identical or different and are $C_2$–$C_6$-alkylene, or $R_1$ is a hexahydro-1,3,5-triazine-1,3,5-triyl group, or if m=4, $R_1$ is a group

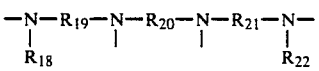

in which $R_{18}$ and $R_{22}$ are identical or different and are as defined for $R_{14}$ and $R_{17}$, while $R_{19}$, $R_{20}$ and $R_{21}$ are identical or different and are $C_2$–$C_6$-alkylene, or $R_1$ is a group

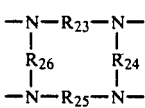

in which $R_{23}$, $R_{24}$, $R_{25}$ and $R_{26}$ are identical or different and are $C_2$–$C_6$-alkylene, $R_2$ is $C_1$–$C_{18}$-alkyl, $C_5$–$C_{18}$-cycloalkyl unsubstituted or substituted by $C_1$–$C_{12}$-alkyl, $C_3$–$C_{18}$-alkenyl, $C_6$–$C_{18}$-aryl unsubstituted or substituted by $C_1$–$C_{12}$-alkoxy, by $C_1$–$C_{12}$-alkyl and/or by —OH, $C_7$–$C_{18}$-aralkyl unsubstituted or substituted by $C_1$–$C_{12}$-alkyl and/or by —OH, or is a group of the formula (II) or, if m is 1 and $R_1$ is a group

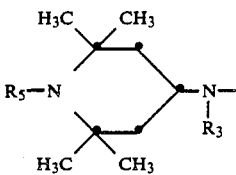

$R_2$ additionally is a group of the formula (III)

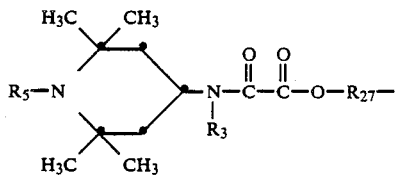

wherein $R_3$ and $R_5$ are as defined above and $R_{27}$ is $C_2$-$C_{12}$-alkylene, $C_6$-$C_{18}$-cycloalkylene or one of the following groups

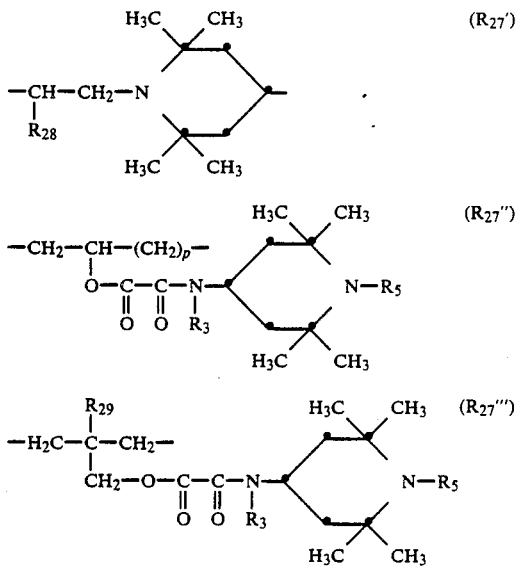

in which $R_{28}$ is hydrogen or $C_1$-$C_4$-alkyl, $R_{29}$ is hydrogen, $C_1$-$C_4$-alkyl or a group

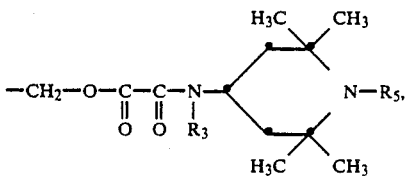

$R_3$ and $R_5$ are as defined above and p is an integer from 1 to 4, at least one group of the formula (II) being present in $R_1$ or $R_2$.

Illustrative examples of the meaning of the various groups are as follows:

for $R_3$ and $R_4$: hydrogen, methyl, ethyl, propyl, isopropyl, butyl, 2-butyl, isobutyl, t-butyl, hexyl, octyl, 2-ethylhexyl, 1,1,3,3-tetramethylbutyl, decyl, dodecyl, tetradecyl, hexadecyl, octadecyl, 2-methoxyethyl, 2-ethoxyethyl, 3-methoxypropyl, 3-ethoxypropyl, 3-butoxypropyl, 3-octyloxypropyl, 3-dodecyloxypropyl, 3-dimethylaminopropyl, 3-diethylaminopropyl, 4-diethylaminobutyl, cyclohexyl, methylcyclohexyl, trimethylcyclohexyl, cyclooctyl, cyclododecyl, allyl, 2-methallyl, 2-butenyl, 2-hexenyl, 10-undecenyl, oleyl, phenyl, methylphenyl, dimethylphenyl, trimethylphenyl, t-butylphenyl, methoxyphenyl, ethoxyphenyl, 3,5-di-butyl-4-hydroxyphenyl, benzyl, methylbenzyl, hydroxybenzyl, 3,5-di-butyl-4-hydroxybenzyl, 2,2,6,6-tetramethylpiperidin-4-yl, 1,2,2,6,6-pentamethylpiperidin-4-yl, 1-allyl-2,2,6,6-tetramethylpiperidin-4-yl, 1-benzyl-2,2,6,6-tetramethyl-piperidin-4-yl and 1-acetyl-2,2,6,6-tetramethylpiperidin-4-yl;

for $R_5$: hydrogen, O., cyanomethyl, methyl, ethyl, propyl, butyl, hexyl, octyl, decyl, dodecyl, allyl, 2-methallyl, 2-butenyl, 2-hexenyl, 10-undecenyl, propargyl, benzyl, methylbenzyl, t-butylbenzyl, hydroxybenzyl, formyl, acetyl, propionyl, butyryl, caproyl, capryloyl, caprinoyl, lauroyl, benzoyl, acryloyl, methacryloyl and crotonyl;

for $R_6$, $R_8$, $R_9$ and $R_{10}$: hydrogen, methyl, ethyl, propyl, isopropyl, butyl, 2-butyl, isobutyl, t-butyl, hexyl, octyl, 2-octyl, 2-ethylhexyl, 1,1,3,3-tetramethylbutyl, decyl, dodecyl, tetradecyl, hexadecyl, octadecyl, cyclopentyl, cyclohexyl, methylcyclohexyl, trimethylcyclohexyl, cyclooctyl, cyclododecyl, allyl, 2-methallyl, 2-butenyl, 2-hexenyl, 10-undecenyl, oleyl, phenyl, methylphenyl, dimethylphenyl, trimethylphenyl, t-butylphenyl, methoxyphenyl, ethoxyphenyl, 3,5-di-t-butyl-4-hydroxyphenyl, benzyl, methylbenzyl, hydroxybenzyl, 3,5-di-t-butyl-4-hydroxybenzyl, 2,2,6,6-tetramethylpiperidin-4-yl, 1,2,2,6,6-pentamethylpiperidin-4-yl, 1-allyl-2,2,6,6-tetramethylpiperidin-4-yl, 1-benzyl-2,2,6,6-tetramethylpiperidin-4-yl and 1-acetyl-2,2,6,6-tetramethylpiperidin-4-yl; for $R_7$: ethylene, propylene, trimethylene, tetramethylene, pentamethylene, 2,2-dimethylpropane-1,3-diyl, 2-methylpentane-2,4-diyl, hexamethylene, decamethylene, dodecamethylene, cyclohexylene, cyclohexylenedimethylene, methylenedicyclohexylene, phenylene and xylylene;

for $R_{11}$, $R_{12}$, $R_{15}$, $R_{16}$, $R_{19}$, $R_{20}$, $R_{21}$, $R_{23}$, $R_{24}$, $R_{25}$ and $R_{26}$: ethylene, propylene, trimethylene, tetramethylene, pentamethylene, hexamethylene and 2-methylpentane-2,4-diyl;

for $R_{13}$: hydrogen, methyl, ethyl, propyl, butyl, hexyl, octyl, decyl, dodecyl, cyclopentyl, cyclohexyl, methylcyclohexyl, trimethylcyclohexyl, cyclooctyl, cyclododecyl, 2,2,6,6-tetramethylpiperidin-4-yl, 1,2,2,6,6-pentamethylpiperidin-4-yl, 1-allyl-2,2,6,6-tetramethylpiperidin-4-yl, 1-benzyl-2,2,6,6-tetramethylpiperidin-4-yl and 1-acetyl-2,2,6,6-tetramethylpiperidin-4-yl; for $R_{14}$, $R_{17}$, $R_{18}$ and $R_{22}$: hydrogen, methyl, ethyl, propyl, isopropyl, butyl, 2-butyl, isobutyl, t-butyl, hexyl, octyl, 2-octyl, 2-ethylhexyl, decyl, dodecyl, tetradecyl, hexadecyl, octadecyl, cyclopentyl, cyclohexyl, methylcyclohexyl, trimethylcyclohexyl, cyclooctyl, cyclododecyl, benzyl, methylbenzyl, t-butylbenzyl, hydroxybenzyl, 3,5-di-t-butyl-4-hydroxybenzyl, 2,2,6,6-tetramethylpiperidin-4-yl, 1,2,2,6,6-pentamethylpiperidin-4-yl, 1-allyl-2,2,6,6-tetramethylpiperidin-4-yl 1-benzyl-2,2,6,6-tetramethylpiperidin-4-yl and 1-acetyl-2,2,6,6-tetramethylpiperidin-4-yl; for $R_2$: methyl, ethyl, propyl, isopropyl, butyl, 2-butyl, isobutyl, t-butyl, hexyl, octyl, 2-ethylhexyl, 1,1,3,3-tetramethylbutyl, decyl, dodecyl, tetradecyl, hexadecyl, octadecyl, cyclohexyl, methylcyclohexyl, trimethylcyclohexyl, cyclooctyl, cyclododecyl, allyl, 2-methallyl, 2-butenyl, 2-hexenyl, 10-undecenyl, oleyl, phenyl, methylphenyl, dimethylphenyl, trimethylphenyl, t-butylphenyl, methoxyphenyl, ethoxyphenyl, 3,5-di-t-butyl-4-hydroxyphenyl, benzyl, methylbenzyl, hydroxybenzyl, 3,5-di-t-butyl-4-hydroxybenzyl, 2,2,6,6-tetramethylpiperidin-4-yl, 1,2,2,6,6-pentamethylpiperidin-4-yl, 1-allyl-2,2,6,6-tetramethylpiperidin-4-yl, 1-benzyl-2,2,6,6-tetramethylpiperidin-4-yl and 1-acetyl-2,2,6,6-tetramethylpiperidin-4-yl, or, if m is 1 and $R_1$ is a group

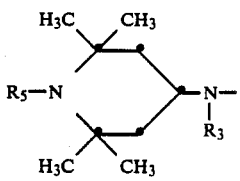

$R_2$ can be a group of the formula (III) in which $R_{27}$ is, for example, ethylene, propylene, trimethylene, tetramethylene, pentamethylene, hexamethylene, 2,2-dimethylpropane-1,3-diyl, 2-methylpentane-2,4-diyl, decamethylene, dodecamethylene, cyclohexylene, cyclohexylenedimethylene, methylenedicyclohexylene or one of the groups $R_{27}'$, $R_{27}''$ and $R_{27}'''$ in which $R_{28}$ and $R_{29}$ can be methyl, ethyl, propyl or butyl and $R_3$ and $R_5$ are as defined above.

If $R_1$ is a heterocyclic group and if m=1, preferred examples are: pyrrolidinyl, piperidino, morpholino, 2,6-di-methylmorpholino, 4-methylpiperazin-1-yl, 3,3,5,5-tetramethylpiperazin-1-yl, hexahydroazepin-1-yl or a radical

in which q is an integer from 3 to 11; if m=2, preferred examples are:

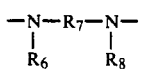

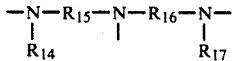

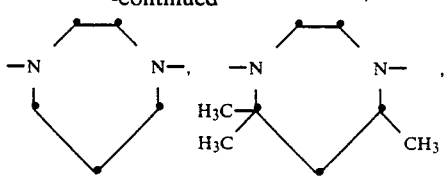

if m=3, $R_1$ can be a hexahydro-1,3,5-triazine-1,3,5-triyl group and if m=4, $R_1$ can be one of the following groups:

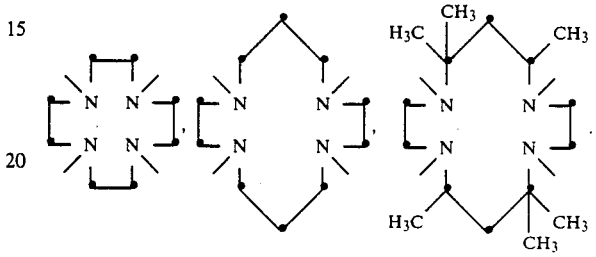

Those compounds of the formula (I) are preferred in which, if m=1, $R_1$ is a group $$-\underset{R_4}{\underset{|}{N}}-R_3$$

in which $R_3$ and $R_4$ are identical or different and are hydrogen, $C_1$–$C_{12}$-alkyl, $C_6$–$C_{12}$-cycloalkyl, allyl, phenyl, benzyl or a group of the formula (II) in which $R_5$ is hydrogen, methyl, allyl, benzyl or acetyl, or $R_1$ is a heterocyclic radical selected from the group consisting of piperidino, morpholino and hexahydroazepin-1-yl; or if m is 2, $R_1$ is a group $$-\underset{R_6}{\underset{|}{N}}-R_7-\underset{R_8}{\underset{|}{N}}-$$

in which $R_6$ and $R_8$ are identical or different and are hydrogen, $C_1$–$C_{12}$-alkyl, $C_6$–$C_9$-cycloalkyl or a group of the formula (II) and $R_7$ is $C_2$–$C_{12}$-alkylene or a group $-R_{11}-X-(R_{12}-X)_{\overline{n}}R_{11}-$ in which $R_{11}$ and $R_{12}$ are identical or different and are $C_2$–$C_6$-alkylene, X is $-O-$ and n is zero, 1 or 2, or $R_1$ is piperazine-1,4-diyl or 5,5,7-trimethylhomopiperazine-1,4-diyl; or if m is 3, $R_1$ is a group $$-\underset{R_{14}}{\underset{|}{N}}-R_{15}-\underset{|}{N}-R_{16}-\underset{R_{17}}{\underset{|}{N}}-$$

in which $R_{14}$ and $R_{17}$ are identical or different and are hydrogen, $C_1$–$C_8$-alkyl, $C_6$–$C_9$-cycloalkyl or a group of the formula (II) and $R_{15}$ and $R_{16}$ are identical or different and are $C_2$–$C_6$-alkylene, or $R_1$ is a hexahydro-1,3,5-triazine-1,3,5-triyl group; or if m is 4, $R_1$ is a group

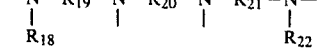

in which $R_{18}$ and $R_{22}$ are identical or different and are hydrogen, $C_1$–$C_8$-alkyl, $C_6$–$C_9$-cycloalkyl or a group of the formula (II) and $R_{19}$, $R_{20}$ and $R_{21}$ are identical or different and are $C_2$–$C_6$-alkylene, or $R_1$ is a group

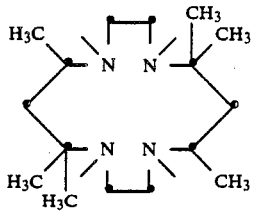

$R_2$ is $C_1$–$C_{12}$-alkyl, $C_6$–$C_9$-cycloalkyl, allyl, phenyl, benzyl or a group of the formula (II) or, if m is 1 and $R_1$ is a group

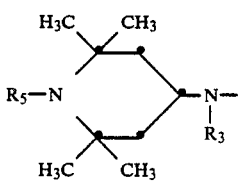

with $R_3$ and $R_5$ being as defined above, $R_2$ additionally is a group of the formula (III) in which $R_{27}$ is $C_2$–$C_6$-alkylene, $C_6$–$C_{12}$-cycloalkylene or one of the groups $R_{27}'$, $R_{27}''$ and $R_{27}'''$ wherein $R_{28}$ is hydrogen or methyl, $R_{29}$ is methyl, ethyl or a group

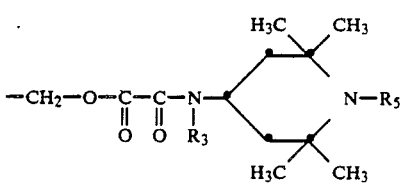

in which $R_3$ and $R_5$ are as defined above and p is 1, with the proviso that at least one group of the formula (II) is present in $R_1$ or $R_2$.

Those compounds of the formula (I) are particularly preferred in which m is 1 or 2 and, if m is 1, $R_1$ is a group

in which $R_3$ is hydrogen, $C_1$–$C_8$-alkyl, cyclohexyl, 2,2,6,6-tetramethylpiperidin-4-yl or 1,2,2,6,6-pentamethylpiperidin-4-yl and $R_4$ is 2,2,6,6-tetramethylpiperidin-4-yl or 1,2,2,6,6-pentamethylpiperidin-4-yl, or, if m is 2, $R_1$ is a group

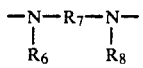

in which $R_6$ and $R_8$ are 2,2,6,6-tetramethylpiperidin-4-yl or 1,2,2,6,6-pentamethylpiperidin-4-yl and $R_7$ is $C_2$–$C_6$-alkylene, or $R_1$ is piperazine-1,4-diyl or 5,5,7-trimethyl-homopiperazine-1,4-diyl, $R_2$ is 2,2,6,6-tetramethylpiperidin-4-yl or 1,2,2,6,6-pentamethylpiperidin-4-yl, or if m is 1 and $R_1$ is a group

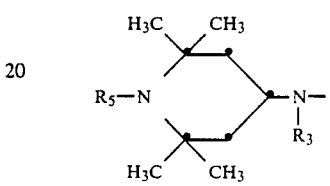

$R_2$ additionally is one of the groups

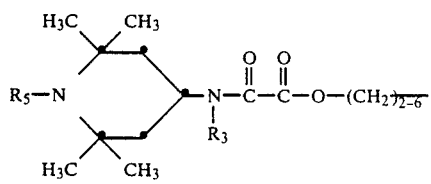

or

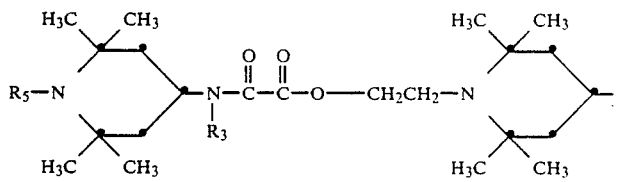

in which $R_3$ is as defined above and $R_5$ is hydrogen or methyl.

Those compounds of the formula (I) wherein m is 1, constitute a preferred embodiment of the invention.

Compounds of the formula (I) in which m is 2 are particularly preferred.

The novel compounds according to the present invention are prepared by various processes in accordance with their chemical characteristics.

In particular, if $R_2$ is a group $R_2'$ defined as $C_1$–$C_{18}$-alkyl, unsubstituted or substituted $C_5$–$C_{18}$-cycloalkyl, $C_3$–$C_{18}$-alkenyl, unsubstituted or substituted $C_6$–$C_{18}$-aryl, unsubstituted or substituted $C_7$–$C_{18}$-aralkyl or a group of the formula (II), the compounds of the formula (I) can be prepared by reacting a compound of the formula (IV)

$$R_1(H)_m \qquad (IV),$$

in which $R_1$ and m are as defined above, with a chlorooxoacetate of the formula (V)

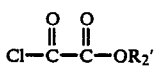 (V)

in which $R'_2$ is as defined above.

A variant of this process is the reaction of a chlorooxoacetamide of the formula (VI) with an alcohol of the formula (VII)

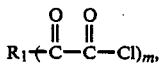 (VI)

 (VII)

in which $R_1$, m and $R'_2$ are as defined above.

If m is 1, $R_1$ is

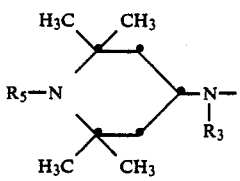

and $R_2$ is a group of the formula (III), the compounds of the formula (I) can be prepared by reacting a chlorooxoacetamide of the formula (VIII)

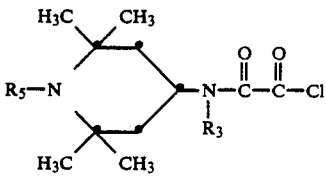 (VIII)

with a compound of the formula (IX), (X) or (XI)

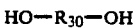 (IX)

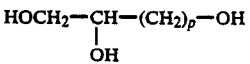 (X)

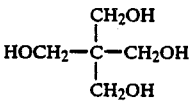 (XI)

in which $R_{30}$ is $C_2$-$C_{12}$-alkylene, $C_6$-$C_{18}$-cycloalkylene or a group

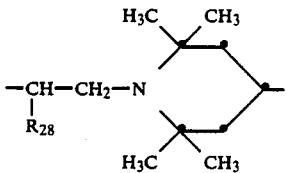

with $R_{28}$ being as defined above, and p is 1 to 4.

An alternative for this last process is the reaction of a compound of the formula (XII)

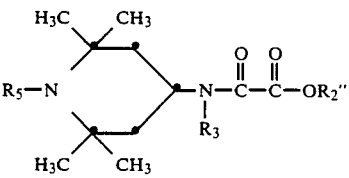 (XII)

in which $R_3$ and $R_5$ are as defined above and $R_2''$ is $C_1$-$C_4$-alkyl, with a compound of the formula (IX), (X) or (XI).

If $R_2$ is a group $R_2'''$ defined as $C_4$-$C_{18}$-alkyl, unsubstituted or substituted $C_5$-$C_{18}$-cycloalkyl, $C_3$-$C_{18}$-alkenyl, unsubstituted or substituted $C_6$-$C_{18}$-aryl, unsubstituted or substituted $C_7$-$C_{18}$-aralkyl or a group of the formula (II), the compounds of the formula (I) can also be prepared by reacting a compound of the formula (XIII)

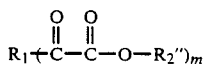 (XIII)

in which $R_1$, m and $R_2''$ are as defined above, with an alcohol of the formula (XIV)

   (XIV)

in which $R_2'''$ is as defined above, with the proviso that $R_2''$ is $C_1$-$C_3$-alkyl if $R_2'''$ is $C_4$-alkyl.

The reactions with chlorooxoacetates (V) and with the chlorooxoacetamides (VI) or (VIII) can be carried out in an inert solvent such as a hydrocarbon, for example n-hexane, or a chlorinated hydrocarbon, for example dichloromethane or dichloroethane, in a stoichiometric molar ratio of the reagents or with an excess of up to 20% of theory of the monofunctional reagents, neutralising the hydrochloric acid liberated in the reactions with an inorganic base, such as sodium or potassium hydroxide or carbonate, in a quantity almost equivalent to the acid, and operating at a temperature between $-30°$ C. and $100°$ C., preferably $-10°$ C. to $50°$ C. If the group of the formula (II) is present, the intermediates of the formulae (V), (VI) and (VIII) are preferably employed in the form of the hydrochlorides. The reactions with the compounds (XII) and (XIII) can be carried out without a solvent or in the presence of an inert solvent as defined above, in a stoichiometric molar ratio of the reagents or with an excess of up to 50% of theory of the monofunctional reagents, at temperatures between $100°$ and $250°$ C., preferably $120°$ C. and $200°$ C., in the presence of a transesterification catalyst, such as an alkali metal or an amide, alcoholate or hydride thereof, or in the presence of titanium(IV) alkoxides.

The intermediates employed for the preparation of the compounds of the formula (I) can be prepared by known processes. In particular, the chlorooxoacetates of the formula (V) can be prepared by reacting oxalyl chloride with an alcohol of the formula (VII), the chlorooxoacetamides (VI) can be prepared by reacting oxalyl chloride with a compound of the formula (IV) and the chlorooxoacetamides (VIII) can be prepared from oxalyl chloride and a compound of the formula (XV)

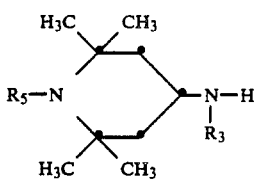

(XV)

The compounds (XII) and (XIII) can be prepared by reacting a compound of the formula (XV) or (IV), respectively, with a $C_1$–$C_4$-alkyl chlorooxoacetate or with a $C_1$–$C_4$-alkyl oxalate.

The intermediates (V), (VI), (VIII), (XII) or (XIII) can be employed directly in the preparation of the compounds of the formula (I), without isolating them from the reaction mixture or after separation or purification.

In order to illustrate the present invention more clearly, several examples of the preparation of the compounds of the formula (I) are described below; these examples are given by way of illustration only and do not imply any restriction.

EXAMPLE 1

Preparation of the compound

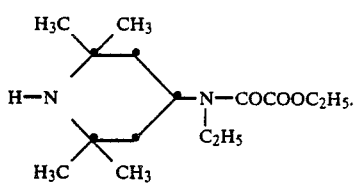

A solution of 75.1 g (0.55 mol) of ethyl chlorooxoacetate in 100 ml of dichloromethane is added slowly to a solution, cooled to 0° C., of 92 g (0.5 mol) of 4-ethylamino-2,2,6,6-tetramethylpiperidine in 500 ml of dichloromethane.

The rate of addition is controlled such that the temperature remains between 0° and 5° C.

The solution is stirred for 3 hours at 10°–15° C. and then cooled to 0° C.

A solution of 22 g (0.55 mol) of sodium hydroxide in 60 ml of water is then added slowly, while maintaining the temperature between 0° and 5° C.

After the end of the addition, the mixture is stirred for 30 minutes at 10°–15° C. The aqueous phase is separated off and the organic phase is washed with water, dried and evaporated.

The residue is crystallised from n-hexane.

This gives 126.8 g of a product of melting point 53°–54° C.

Analysis for $C_{15}H_{28}N_2O_3$: Calculated: C 63.35%; H 9.91%; N 9.85%. Found: C 63.60%; H 9.88%; N 9.95%.

EXAMPLE 2-5

Repeating the procedure described in Example 1, but employing the appropriate intermediates, the following compounds of the formula (I) are prepared.

| Example No. | Product | Melting point (°C.) |
|---|---|---|
| 2 | (structure: 2,2,6,6-tetramethylpiperidin-4-yl-NH linked to piperidinyl-N—COCOOC₂H₅) | 150.9 |
| 3 | H₅C₂OOC—CO—N———(CH₂)₆———N—CO—COOC₂H₅ (bis-tetramethylpiperidinyl) | 131.7 |
| 4 | H₅C₂OOC—CO—N———(CH₂)₃———N—CO—COOC₂H₅ (bis-tetramethylpiperidinyl) | 132.9 |

-continued

| Example No. | Product | Melting point (°C.) |
|---|---|---|
| 5 | H₅C₂OOC—CO—N[piperidine]—(CH₂)₂—N[piperidine]—CO—COOC₂H₅ | 190.9 |

EXAMPLE 6

Preparation of the compound

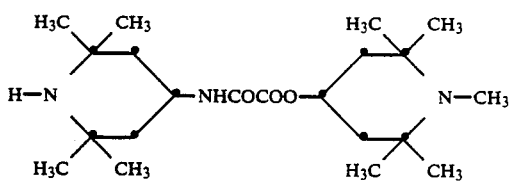

(a) Preparation of 1,2,2,6,6-pentamethylpiperidin-4yl chlorooxoacetate hydrochloride:

A solution of 137 g (0.8 mol) of 4-hydroxy-1,2,2,6,6-pentamethylpiperidine in 2000 ml of n-hexane is slowly added to a solution, cooled to −30° C., of 203.2 g (1.6 mol) of oxalyl chloride in 2300 ml of n-hexane, while maintaining the above temperature.

The mixture is then stirred for 12 hours, while allowing the temperature to rise gradually to about 20° C.

The precipitate obtained is separated off by filtration and dried at 25° C. in vacuo (26.7 mbar).

This gives 235 g of product which can be used directly for the subsequent reactions.

Analysis for $C_{12}H_{21}Cl_2NO_3$: Calculated: Cl 23.77%. Found: Cl 23.58%.

(b) Preparation of 1,2,2,6,6-pentamethylpiperidin-4yl N-2,2,6,6-tetramethylpiperidin-4-yl-aminooxoacetate:

A solution of 18.7 g (0.12 mol) of 4-amino-2,2,6,6-tetramethylpiperidine in 40 ml of dichloromethane is added slowly to a solution, cooled to about 0° C., of 29.8 g (0.1 mol) of 1,2,2,6,6-pentamethylpiperidin-4-yl chlorooxoacetate hydrochloride in 100 ml of dichloromethane, while maintaining the temperature at 0°–5° C.

The mixture is stirred for 1 hour at 0°–5° C. and for 4 hours at ambient temperature.

After cooling again to 0°–5° C., a solution of 10 g (0.25 mol) of sodium hydroxide in 30 ml of water is added.

After the end of the addition, the mixture is stirred for 1 hour at 0°–5° C. and for 1 hour at ambient temperature.

The organic phase is separated off, washed with water, dried and evaporated.

The residue is crystallised from n-hexane.

This gives 34.7 g of product of melting point 142°–143° C.

Analysis for $C_{21}H_{39}N_3O_3$: Calculated: C 66.10%; H 10.30%; N 11.01%. Found: C 66.79%; H 10.34%; N 11.12%.

EXAMPLE 7

Preparation of the compound

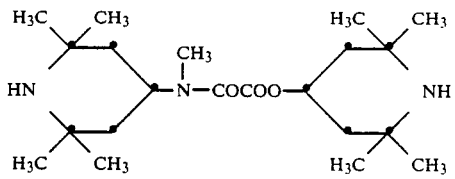

(a) Preparation of 2,2,6,6-tetramethylpiperidin-4-yl chlorooxoacetate hydrochloride:

67.1 g (0.52 mol) of oxalyl chloride are added to a mixture of 51.1 g (0.26 mol) of 4-hydroxy-2,2,6,6-tetramethylpiperidine hydrochloride and 500 ml of dichloroethane, and the mixture is heated under reflux for 6 hours.

The solution thus obtained is evaporated in vacuo (26.7 mbar) and the residue (73.5 g) can be employed directly for the subsequent reactions.

Analysis for $C_{11}H_{19}Cl_2NO_3$: Calculated: Cl 24.95%. Found: Cl 24.88%.

(b) Preparation of 2,2,6,6-tetramethylpiperidin-4-yl N-methyl-N-2,2,6,6-tetramethylpiperidin-4-yl-aminooxoacetate:

A solution of 20.4 g (0.12 mol) of 4-methylamino-2,2,6,6-tetramethylpiperidine in 40 ml of dichloromethane is added slowly to a solution, cooled to about 0° C., of 28.4 g (0.1 mol) of 2,2,6,6-tetramethylpiperidin-4-yl chlorooxoacetate hydrochloride in 100 ml of dichloromethane, while maintaining the temperature at 0° C.

The mixture is stirred for 1 hour 0°–5° C. and for 4 hours at ambient temperature. After cooling again to about 0° C., a solution of 10 g (0.25 mol) of sodium hydroxide in 30 ml of water is added. After the end of the addition, the mixture is stirred for 1 hour at 0°–5° C. and for 1 hour at ambient temperature.

The organic phase is separated off, washed with water, dried and evaporated.

The residue is crystallised from n-hexane.

This gives 28.5 g of product of melting point 97°–98° C.

Analysis for $C_{21}H_{39}N_3O_3$: Calculated: C 66.11%; H 10.30%; N 11.01%. Found: C 66.09%; H 10.28%; N 10.88%.

EXAMPLES 8–24

Repeating the procedures described in Examples 6 and 7, but employing the appropriate intermediates, the following compounds of the formula (I) are prepared.

| Example No. | Product | m.p. (°C.) |
|---|---|---|
| 8 | (structure with central N-CH₃ bridging two 2,2,6,6-tetramethylpiperidine rings via -COCOO-, left ring HN, right ring N-CH₃) | 80-81 |
| 9 | (structure with central N-C₂H₅ bridging two 2,2,6,6-tetramethylpiperidine rings via -COCOO-, left ring HN, right ring NH) | 103-104 |
| 10 | (structure with central N-C₂H₅ bridging two 2,2,6,6-tetramethylpiperidine rings via -COCOO-, left ring HN, right ring N-CH₃) | 88-89 |
| 11 | (structure with central N-C₄H₉ bridging two 2,2,6,6-tetramethylpiperidine rings via -COCOO-, left ring HN, right ring N-CH₃) | resin |
| 12 | (structure with central N-cyclohexyl bridging two 2,2,6,6-tetramethylpiperidine rings via -COCOO-, left ring HN, right ring NH) | 147 |
| 13 | (structure with central N-(2,2,6,6-tetramethylpiperidin-4-yl, NH) bridging two 2,2,6,6-tetramethylpiperidine rings via -COCOO-, left ring HN, right ring N-CH₃) | 178-179 |
| 14 | (structure with central N-C₈H₁₇ bridging two 2,2,6,6-tetramethylpiperidine rings via -COCOO-, left ring HN, right ring N-CH₃) | Oil |

-continued

| Example No. | Product | m.p. (°C.) |
|---|---|---|
| 15 | | 158–159 |
| 16 | | 217–218 |
| 17 | | 227–228 |
| 18 | | 149–150 |
| 19 | | 170–171 |
| 20 | | 116–117 |

| Example No. | Product | m.p. (°C.) |
|---|---|---|
| 21 | | 210–211 |
| 22 | | 224–225 |
| 23 | | 121–122 |
| 24 | | 136–137 |

EXAMPLE 25

Preparation of the compound

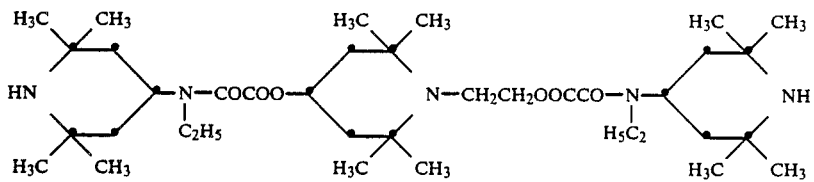

A solution of 39.1 g (0.31 mol) of oxalyl chloride in 50 ml of dichloroethane is added slowly to a solution, cooled to 0° C., of 39.6 g (0.15 mol) of 4-ethylamino-2,2,6,6-tetramethylpiperidine dihydrochloride in 250 ml of dichloroethane, while maintaining the temperature between 0° and 10° C.

The mixture is heated for 4 hours under reflux, and the solvent and the excess oxalyl chloride are distilled off in vacuo (26.7 mbar).

The crude product thus obtained, consisting of N-ethyl-N-(2,2,6,6-tetramethylpiperidin-4-yl)-chlorooxoacetamide hydrochloride, is dissolved in 200 ml of dichloroethane.

14.1 g (0.07 mol) of 1-(2-hydroxyethyl)-4-hydroxy-2,2,6,6-tetramethylpiperidine are added to the solution thus obtained at a temperature of 15°–20° C.

The mixture is heated under reflux for 6 hours. After cooling again to 0°–5° C., a solution of 13.2 g (0.33 mol) of sodium hydroxide in 50 ml of water is added.

The mixture is stirred for 1 hour at ambient temperature.

The phases are separated. The organic phase is washed with water, dried and evaporated.

This gives 40.5 g of product of melting point 141°–142° C.

Analysis for $C_{37}H_{67}N_5O_6$: Calculated: C 65.55%; H 9.96%; N 10.33%. Found: C 65.19%; H 9.97%; N 10.27%.

EXAMPLE 26

Preparation of the compound

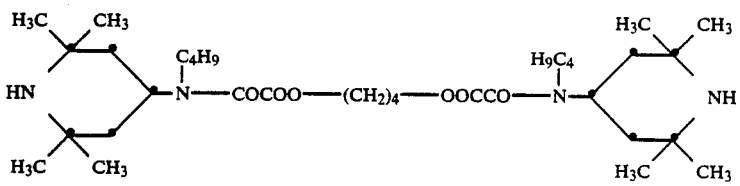

4.05 g (0.045 mol) of 1,4-butanediol and 1 ml of titanium tetraisopropylate are added to 31.2 g (0.1 mol) of ethyl N-butyl-N-2,2,6,6-tetramethylpiperidin-4-yl-aminooxoacetate prepared from 4-butylamino-2,2,6,6-tetramethylpiperidine and ethyl chlorooxoacetate by the procedure described in Example 1.

The mixture is heated for 4 hours at 140°-150° C. under a gentle nitrogen stream with elimination of the ethanol of reaction (5.3 ml) and then for 1 hour at 150° C. under 6.67 mbar.

After cooling, the reaction mixture is dissolved in 100 ml of dichloroethane, and the solution is washed with water, dried and evaporated.

The residue is crystallised from n-hexane. This gives 17.3 g of product of melting point 64° C.

Analysis for $C_{34}H_{62}N_4O_6$: Calculated: C 65.56%; H 10.03%; N 8.99%. Found: C 65.74%; H 10.11%; N 8.98%.

EXAMPLES 27-33

Repeating the procedure of Example 26, but employing the reagents indicated, the following compounds of formula (I) are prepared.

| Ex. No. | Reagents | Product | m.p. (°C.) |
|---|---|---|---|
| 27 | [structure with N—COCOOC₂H₅ and HO(CH₂)₆OH] | [structure with —N—COCOO(CH₂)₃— ]₂ | resin |
| 28 | [structure with N—COCOOC₂H₅ and HO—piperidine—N—CH₂CH₂OH] | [structure with —N—COCOO— ]₂ piperidine—NCH₂CH₂— | 56–57 |
| 29 | [structure with —N—COCOOC₂H₅ ]₂ and n-C₄H₉OH | [structure with —N—COCOOC₄H₉ ]₂ | 88–89 |
| 30 | [structure with —N—COCOOC₂H₅ ]₂ and n-C₈H₁₇OH | [structure with —N—COCOOC₈H₁₇ ]₂ | 89–90 |

| Ex. No. | Reagents | Product | m.p. (°C.) |
|---|---|---|---|
| 31 | H₃C, CH₃ ring with HN and N—COCOOC₂H₅, C₂H₅ substituent; (H₃C)₂—C—(CH₂OH)₂ | [same ring—N—COCOO—CH₂—C(CH₃)₂—CH₂—]₂ | resin |
| 32 | H₃C, CH₃ ring with HN and N—COCOOC₂H₅, C₂H₅ substituent; H₅C₂—C—(CH₂OH)₃ | [same ring—N—COCOO—CH₂—C(C₂H₅)(CH₂)—CH₂—]₃ | resin |
| 33 | H₃C, CH₃ ring with HN and N—COCOOC₂H₅, C₂H₅ substituent; C—(CH₂OH)₄ | [same ring—N—COCOO—CH₂—C(CH₂)(CH₂)—CH₂—]₄ | resin |

As mentioned at the outset, the compounds of the formula (I) are very effective in improving the light stability, heat stability and oxidation stability of organic material, especially synthetic polymers, for example high-density and low-density polyethylene, polypropylene, ethylene/propylene copolymers, ethylene/vinyl acetate copolymers, polybutadiene, polyisoprene, polystyrene, butadiene/styrene copolymers, vinyl chloride/vinylidene chloride polymers and copolymers, polyoxymethylene, polyphenylene oxide, polyurethanes, saturated and unsaturated polyesters, polyamides, polycarbonates, polyacrylates, alkyd resins and epoxide resins.

A further embodiment of the present invention is an organic material containing a compound of the formula (I). The organic material is preferably a synthetic polymer. Polyethylene and polypropylene are particularly preferred.

The compounds of the formula (I) can be mixed with organic material, for example synthetic polymers, in various proportions depending on the nature of the polymer, the end use and the presence of other additives.

In general, it is advantageous to employ from 0.01 to 5% by weight of the compounds of the formula (I), relative to the weight of the polymers, preferably from 0.05 to 1%.

The compounds of the formula (I) can be incorporated into the polymeric materials by various processes, such as dry blending in the form of powders, or wet mixing in the form of solutions or suspensions, or in the form of a masterbatch; in these operations, the polymer can be employed in the form of powder or granules or in the form of a solution, a suspension or a latex.

The organic material stabilised with the products of the formula (I) can be used for the preparation of moulded articles, films, tapes, fibres, monofilaments, surface-coatings and the like.

If desired, other additives, for example antioxidants, ultraviolet absorbers, nickel stabilisers, pigments, fillers, plasticisers, antistatic agents, flameproofing agents, lubricants, corrosion inhibitors and metal deactivators, can be added to the mixtures of the compounds of the formula (I) with the polymers. Examples of additives which can be mixed with the compounds of the formula (I) are, in particular:

1. Antioxidants 1.1. Alkylated monophenols, for example,
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example,
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkyliden-bisphenols, for example,
2,2'-methylene-bis-(6-tert.butyl-4-methylphenol)
2,2'-methylene-bis-(6-tert.butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]

2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl)-butane
2,6-bis-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)-butyrate]
bis-(3-tert.butyl-4-hydroxy-5-methylphenyl)-dicyclopentadiene
bis-[2-(3'-tert.butyl-2'-hydroxy-5'-methyl-benzyl)-6-tert.butyl-4-methylphenyl]-terephthalate.

1.5. Benzylcompounds, for example,
1,3,5-tri-(3,5-di-tert.butyl-4-hydroxybenzyl)-2,4,6-trimethylbenzene
bis-(3,5-di-tert.butyl-4-hydroxybenzyl) sulfide
3,5-di-tert.butyl-4-hydroxybenzylmercaptoacetic acid isooctyl ester
bis-(4-tert.butyl-3-hydroxy-2,6-dimethylbenzyl)dithiol terephthalate
1,3,5-tris-(3,5-di-tert.butyl-4-hydroxybenzyl) isocyanurate
1,3,5-tris-(4-tert.butyl-3-hydroxy-2,6-dimethylbenzyl) isocyanurate
3,5-di-tert.butyl-4-hydroxybenzyl-phosphonic acid dioctadecyl ester
3,5-di-tert.butyl-4-hydroxybenzyl-phosphonic acid monoethyl ester calcium salt 1.6. Acylaminophenols, for example,
anilide of 4-hydroxy-lauric acid
anilide of 4-hydroxy-stearic acid
2,4-bis-octylmercapto-6-(3,5-tert.butyl-4-hydroxyanilino)-s-triazine
octyl-N-(3,5-di-tert.butyl-4-hydroxyphenyl)-carbamate 1.7. Esters of β-(3,5-di-tert.butyl-4-hydroxyphenyl)-propionic acid with monohydric or polyhydric alcohols, for example,
methanol
octadecanol
1,6-hexanediol
neopentylglycol
thiodiethyleneglycol
diethyleneglycol
triethyleneglycol
pentaerythritol
tris-(hydroxyethyl) isocyanurate
N,N'-bis(hydroxyethyl) oxalic acid diamide 1.8. Ester of β-(5-tert.butyl-4-hydroxy-3-methylphenyl)propionic acid with monohydric or polyhydric alcohols, for example,
methanol
octadecanol
1,6-hexanediol
neopentylglycol
thiodiethyleneglycol
diethyleneglycol
triethyleneglycol
pentaerytritol
tris-(hydroxethyl) isocyanurate
N,N'-bis(hydroxyethyl) oxalic acid diamide 1.9. Amides of β-(3,5-di-tert.butyl-4-hydroxyphenyl)-propionic acid for example,
N,N'-bis-(3,5-di-tert.butyl-4-hydroxyphenylpropionyl)-hexamethylendiamine
N,N'-bis-(3,5-di-tert.butyl-4-hydroxyphenylpropionyl)-trimethylendiamine
N,N'-bis-(3,5-di-tert.butyl-4-hydroxyphenylpropionyl)-hydrazine 2. UV absorbers and light stabilisers 2.1. 2-(2'-Hydroxyphenyl)-benzotriazoles, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 4'-octoxy-, 3',5'-di-tert.amyl-, 3',5'-bis-(α,α-dimethylbenzyl)-derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxyderivative.

2.3. Esters of optionally substituted benzoic acids for example, phenyl salicylate, 4-tert.butyl-phenyl salicylate, octylphenyl salicylate, dibenzoylresorcinol, bis-(4-tert.butylbenzoyl)-resorcinol, benzoylresorcinol,3,5-di-tert.-butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxycinnamic acid methyl ester or butyl ester, α-carbomethoxy-p-methoxycinnamic acid methyl ester, N-(β-carbomethoxy-β-cyanovinyl)-2-methylindoline.

2.5 Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxypyrazole, optionally with additional ligands.

2.6. Sterically hindered amines, for example, bis-(2,2,6,6-tetramethylpiperidyl)sebacate bis-(1,2,2,6,6-pentamethylpiperidyl)sebacate n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-bis-(2,2,6,6-tetramethylpiperidyl)-hexamethylendiamine and 4-tert.octylamino-2,6-dichloro-1,3,5-s-triazine, tris-(2,2,6,6-tetramethylpiperidyl)nitrilotriacetate, tetrakis-(2,2,6,6-tetramethyl-4-piperidyl) 1,2,3,4-butane tetracarboxylate, 1,1'(1,2-ethanediyl)-bis-(3,3,5,5-tetramethylpiperazinone).

2.7. Oxalic acid diamides, for example, 4,4'-dioctyloxy oxanilide, 2,2'-di-octyloxy-5,5'-di-tert.butyl oxanilide, 2,2'-di-dodecyloxy-5,5'-di-tert.butyl oxanilide, 2-ethoxy-2'-ethyl oxanilide, N,N'-bis-(3-dimethylaminopropyl)-oxalamide, 2-ethoxy-5-tert.butyl-2'-ethyloxanilide and its mixture with 2-ethoxy-2'-ethyl-5,4'-di-tert.butyloxanilide and mixtures of ortho-and para-methoxy- as well as of o- and p-ethoxy-disubstituted oxanilides.

3. Metal deactivators, for example, N,N'-diphenyl oxalic acid diamide, N-salicylal-N'-salicyloylhydrazine, N,N'-bis-(salicyloyl)hydrazine, N,N'-bis-(3,5-di-tert.butyl-4-hydroxyphenylpropionyl)hydrazine, 3-salicyloylamino-1,2,4-triazole, bis-(benzylidene)oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl pentaerythritol diphosphite, tris-(2,4-di-tert.butylphenyl) phosphite, di-isodecyl pentaerythritol diphosphite, di-(2,4-di-tert.butylphenyl)pentaerythritol diphosphite, tristearyl-sorbitol triphosphite, tetrakis-(2,4-di-tert-.butylphenyl) 4,4'-biphenylene diphosphonite.

5. Compounds which destroy peroxide, for example, esters of β-thiodipropionic acid, for example the lauryl, stearyl, myristyl or tridecyl esters, mercaptobenzimidazole or the zinc salt of 2-mercaptobenzimidazole, zinc-dibutyl-dithiocarbamate, dioctadecyldisulfide, pentaerythritol tetrakis-(β-dodecylmercapto)-propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

The efficiency, as stabilisers, of the products prepared according to the present invention is illustrated by the examples which follow, in which some products obtained in the preparation examples are used for stabilising polypropylene tapes and sheets.

EXAMPLE 34

2 g of each of the compounds indicated in Table 1, 1 g of pentaerythritol tetrakis-3-(3,5-di-t-butyl-4-hydroxy-phenyl)propionate and 1 g of calcium stearate are mixed in a powder mixer with 1,000 g of polypropylene powder of melt index 3 ( ® Propathene HF 22, a product of Imperial Chemical Industries).

The mixtures obtained are extruded at a temperature of 180°–220° C., to give polymer granules which are then converted into stretched tapes of 50μ thickness and 2.5 mm width, under the following working conditions:

Extruder temperature: 220°–240° C.
Head temperature: 240° C.
Stretch ratio: 1:6.

The tapes thus prepared are exposed, mounted on a white card, in a 65 WR model Weather-Ometer (ASTM G 27-70), with a black panel temperature of 63° C.

The residual tenacity is measured on samples, taken after various times of exposure to light, by means of a constant-speed tensometer; the exposure time in hours ($T_{50}$) needed to halve the initial tenacity is then calculated.

For comparison, tapes prepared under the same conditions as indicated above, but without the addition of the compounds of the invention, are also exposed. The results obtained are shown in Table 1.

TABLE 1

| Stabiliser | $T_{50}$ (hours) |
|---|---|
| without stabiliser | 216 |
| Compound of Example 2 | 2,160 |
| Compound of Example 3 | 1,780 |
| Compound of Example 7 | 1,920 |
| Compound of Example 8 | 2,420 |
| Compound of Example 9 | 1,910 |
| Compound of Example 10 | 2,800 |
| Compound of Example 11 | 3,390 |
| Compound of Example 13 | 3,100 |
| Compound of Example 14 | 2,150 |
| Compound of Example 17 | 1,900 |
| Compound of Example 18 | 2,000 |
| Compound of Example 19 | 2,200 |
| Compound of Example 20 | 2,490 |
| Compound of Example 21 | 2,410 |
| Compound of Example 22 | 2,350 |
| Compound of Example 24 | 2,210 |
| Compound of Example 27 | 1,740 |
| Compound of Example 28 | 1,770 |
| Compound of Example 29 | 2,060 |
| Compound of Example 30 | 2,050 |

EXAMPLE 35

1.0 g of each of the products indicated in Table 2, 1 g of pentaerythritol tetrakis-3-(3,5-di-t-butyl-4-hydroxyphenyl)propionate, 1 g of calcium stearate, 1 g of blue phtalocyanine and 1,000 g of polypropylene powder of melt index 3 ( ® Propathene HF 22, product of Imperial Chemical Industries) are intimately mixed in a slow mixer.

The mixtures obtained are extruded at a temperature of 200°–220° C. to give polymer granules which are then converted into 2 mm thick sheets by die extrusion at 250° C.

The sheets thus obtained are exposed in a 65 WR model Weather-Ometer (ASTM G 27-70), with a black panel temperature of 63° C., up to the onset of surface embrittlement (chalking). For comparison, a polypropylene sheet prepared under the same conditions as indicated above, but without the addition of the compounds of the invention, is also exposed.

The exposure time (in hours) required for such an onset of embrittlement is indicated in Table 2.

TABLE 2

| Stabiliser | Surface embrittlement time (hours) |
|---|---|
| Without stabiliser | 510 |
| Compound of Example 2 | 2,300 |
| Compound of Example 7 | 2,700 |
| Compound of Example 8 | 2,500 |
| Compound of Example 9 | 3,000 |
| Compound of Example 10 | 2,650 |
| Compound of Example 11 | 3,500 |
| Compound of Example 20 | 2,700 |
| Compound of Example 21 | 2,400 |
| Compound of Example 22 | 2,490 |
| Compound of Example 28 | 3,000 |
| Compound of Example 30 | 2,200 |

What we claim is:
1. A compound of the formula

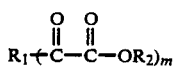

wherein m is an integer from 1 to 4 and, if m=1, $R_1$ is a group

in which $R_3$ and $R_4$ are identical or different and are hydrogen, $C_1$-$C_{18}$-alkyl, $C_2$-$C_6$-alkyl substituted by $C_1$-$C_{18}$-alkoxy or by $C_2$-$C_{18}$-dialkylamino, $C_5$-$C_{18}$-cycloalkyl, $C_3$-$C_{18}$-alkenyl, $C_6$-$C_{18}$-aryl unsubstituted or substituted by $C_1$-$C_{12}$-alkoxy, by $C_1$-$C_{12}$-alkyl and/or by —OH, $C_7$-$C_{18}$-aralkyl unsubstituted or substituted by $C_1$-$C_{12}$-alkyl and/or by —OH or are a group of the formula (II)

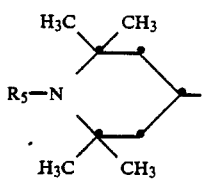

wherein $R_5$ is hydrogen, 0°, cyanomethyl, $C_1$-$C_{12}$-alkyl, $C_3$-$C_{12}$-alkenyl or $C_3$-$C_{12}$-alkynyl, $C_7$-$C_{12}$-aralkyl unsubstituted or substituted by $C_1$-$C_{12}$-alkyl, or is $C_1$-$C_{12}$-acyl, or $R_1$ is a 5-membered to 13-membered heterocyclic radical containing at least one nitrogen atom being linked to the —COCOOR$_2$ radical, said heterocyclic radical being selected from the group consisting of pyrrolidinyl, piperidino, morpholino, 2,6-dimethylmorpholino, 4-methylpiperazin-1-yl, 3,3,5,5-tetramethylpiperazin-1-yl, hexahydroazepin-1-yl and a radical of the formula

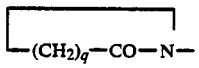

with q=3–11; or if m=2, $R_1$ is a group

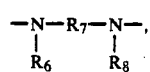

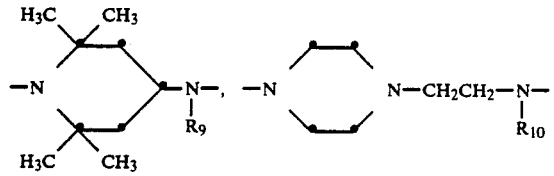

in which $R_6$, $R_8$, $R_9$ and $R_{10}$ are identical or different and are hydrogen, $C_1$-$C_{18}$-alkyl, $C_5$-$C_{18}$-cycloalkyl unsubstituted or substituted by $C_1$-$C_{12}$-alkyl, $C_3$-$C_{18}$-alkenyl, $C_6$-$C_{18}$-aryl unsubstituted or substituted by $C_1$-$C_{12}$-alkoxy, by $C_1$-$C_{12}$-alkyl and/or by—OH, $C_7$-$C_{18}$-aralkyl unsubstituted or substituted by $C_1$-$C_{12}$-alkyl and/or by —OH or are a group of the formula (II) and $R_7$ is $C_2$-$C_{18}$-alkylene, $C_6$-$C_{18}$-cycloalkylene, $C_6$-$C_{18}$-arylene, $C_7$-$C_{18}$-aralkylene or a group —$R_{11}$—X—($R_{12}$—X)$_n$—$R_{11}$—, where $R_{11}$ and $R_{12}$ are identical or different and are $C_2$-$C_6$-alkylene and X is —O—or

$R_{13}$ is hydrogen, $C_1$-$C_{12}$-alkyl, $C_5$-$C_{12}$-cycloalkyl unsubstituted or substituted by $C_1$-$C_{12}$-alkyl, or is a group of the formula (II) and n is zero, 1 or 2, or $R_1$ is a 5-membered to 7-membered divalent heterocyclic group containing 2 nitrogen atoms being linked to the —COCOOR$_2$ radicals, said divalent heterocyclic group being selected from the group consisting of

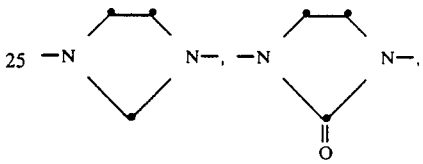

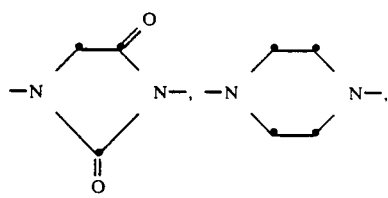

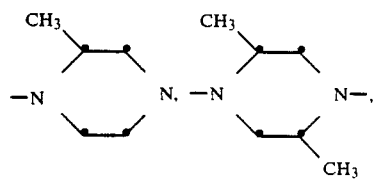

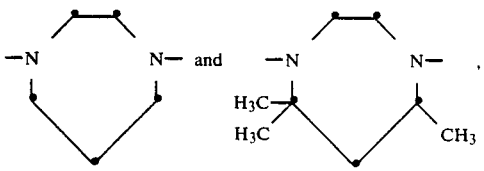

or if m=3, $R_1$ is a group

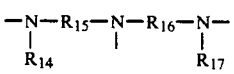

in which $R_{14}$ and $R_{17}$ are identical or different and are hydrogen, $C_1$-$C_{18}$-alkyl, $C_5$-$C_{12}$-cycloalkyl unsubstituted or substituted by $C_1$-$C_{12}$-alkyl, $C_7$-$C_{18}$-aralkyl unsubstituted or substituted by $C_1$-$C_{12}$-alkyl and/or by —OH or are a group of the formula (II) and $R_{15}$ and $R_{16}$ are identical or different and are $C_2$-$C_6$-alkylene, or $R_1$ is a hexahydro-1,3,5-triazine-1,3,5-triyl group, or if m=4, $R_1$ is a group

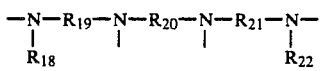

in which $R_{18}$ and $R_{22}$ are identical or different and are as defined for $R_{14}$ and $R_{17}$, while $R_{19}$, $R_{20}$ and $R_{21}$ are identical or different and are $C_2$-$C_6$-alkylene, or $R_1$ is a group

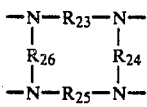

in which $R_{23}$, $R_{24}$, $R_{25}$ and $R_{26}$ are identical or different and are $C_2$-$C_6$-alkylene; $R_2$ is $C_1$-$C_{18}$-alkyl, $C_5$-$C_{18}$-cycloalkyl unsubstituted or substituted by $C_1$-$C_{12}$-alkyl, $C_3$-$C_{18}$-alkenyl, $C_6$-$C_{18}$-aryl unsubstituted or substituted by $C_1$-$C_{12}$-alkoxy, by $C_1$-$C_{12}$-alkyl and/or by —OH, $C_7$-$C_{18}$-aralkyl unsubstituted or substituted by $C_1$-$C_{12}$-alkyl and/or by —OH, or is a group of the formula (II) or, if m is 1 and $R_1$ is a group

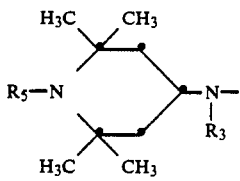

$R_2$ additionally is a group of the formula (III)

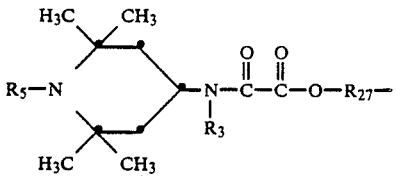
(III)

wherein $R_3$ and $R_5$ are as defined above and $R_{27}$ is $C_2$-$C_{12}$-alkylene, $C_6$-$C_{18}$-cycloalkylene or one of the following groups

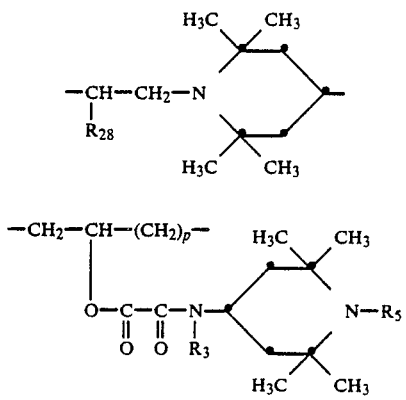

in which $R_{28}$ is hydrogen or $C_1$-$C_4$-alkyl, $R_{29}$ is hydrogen, $C_1$-$C_4$-alkyl or a group

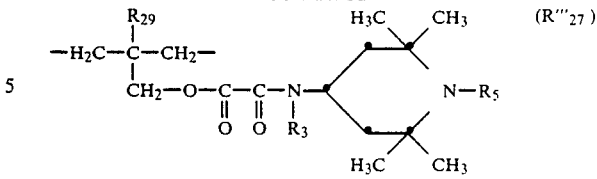

$R_3$ and $R_5$ are as defined in this claim and p is an integer from 1 to 4, at least one group of the formula (II) being present in $R_1$ or $R_2$.

2. A compound of the formula (I) according to claim 1, in which, if m is 1, $R_1$ is a group

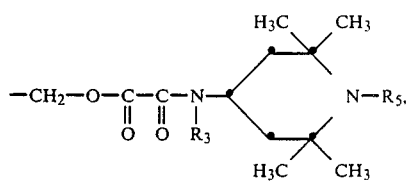

in which $R_3$ and $R_4$ are identical or different and are hydrogen, $C_1$-$C_{12}$-alkyl, $C_6$-$C_{12}$-cycloalkyl, allyl, phenyl, benzyl or a group of the formula (II) in which $R_5$ is hydrogen, methyl, allyl, benzyl or acetyl, or $R_1$ is a heterocyclic radical selected from the group consisting of piperidino, morpholino and hexahydroazepin-1-yl; or if m is 2, $R_1$ is a group

in which $R_6$ and $R_8$ are identical or different and are hydrogen, $C_1$-$C_{12}$-alkyl, $C_6$-$C_9$-cycloalkyl or a group of the formula (II) and $R_7$ is $C_2$-$C_{12}$-alkylene or a group —$R_{11}$—X—($R_{12}$—X)$_n$—$R_{11}$— in which $R_{11}$ and $R_{12}$ are identical or different and are $C_2$-$C_6$-alkylene, X is —O— and n is zero, 1 or 2, or $R_1$ is piperazine-1,4-diyl or 5,5,7-trimethyl-homopiperazine-1,4-diyl; or if m is 3, $R_1$ is a group

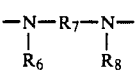

in which $R_{14}$ and $R_{17}$ are identical or different and are hydrogen, $C_1$-$C_8$-alkyl, $C_6$-$C_9$-cycloalkyl or a group of the formula (II) and $R_{15}$ and $R_{16}$ are identical or different and are $C_2$-$C_6$-alkylene, or $R_1$ is a hexahydro-1,3,5-triazine-1,3,5-triyl group; or if m is 4, $R_1$ is a group

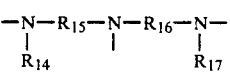

in which $R_{18}$ and $R_{22}$ are identical or different and are hydrogen, $C_1$-$C_8$-alkyl, $C_6$-$C_9$-cycloalkyl or a group of the formula (II) and $R_{19}$, $R_{20}$ and $R_{21}$ are identical or different and are $C_2$-$C_6$-alkylene, or $R_1$ is a group

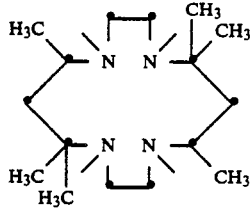

$R_2$ is $C_1$-$C_{12}$-alkyl, $C_6$-$C_9$-cycloalkyl, allyl, phenyl, benzyl or a group of the formula (II) or, if m is 1 and $R_1$ is a group

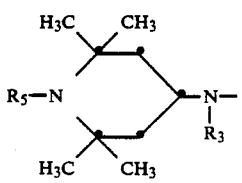

with $R_3$ and $R_5$ being as defined in this claim, $R_2$ additionally is a group of the formula (III) in which $R_{27}$ is $C_2$-$C_6$-alkylene, $C_6$-$C_{12}$-cycloalkylene or one of the groups $R_{27}'$, $R_{27}''$ and $R_{27}'''$ being as defined in claim 1, wherein $R_{28}$ is hydrogen or methyl, $R_{29}$ is methyl, ethyl or a group

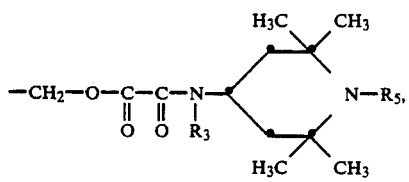

$R_3$ and $R_5$ are as defined in this claim and p is 1, with the proviso that at least one group of the formula (II) is present in $R_1$ or $R_2$.

3. A compound of the formula (I) according to claim 1, in which m is 1 or 2 and, if m is 1, $R_1$ is a group

in which $R_3$ is hydrogen, $C_1$-$C_8$-alkyl, cyclohexyl, 2,2,6,6-tetramethylpiperidin-4-yl or 1,2,2,6,6-pentamethylpiperidin-4-yl and $R_4$ is 2,2,6,6-tetramethylpiperidin-4-yl or 1,2,2,6,6-pentamethylpiperidin-4-yl, or if m is 2, $R_1$ is a group

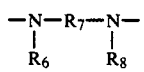

in which $R_6$ and $R_8$ are 2,2,6,6-tetramethylpiperidin-4-yl or 1,2,2,6,6-pentamethylpiperidin-4-yl and $R_7$ is $C_2$-$C_6$-alkylene, or $R_1$ is piperazine-1,4-diyl or 5,5,7-trimethylhomopiperazine-1,4-diyl, $R_2$ is 2,2,6,6-tetramethylpiperidin-4-yl or 1,2,2,6,6-pentamethylpiperidin-4-yl, or if m is 1 and $R_1$ is a group

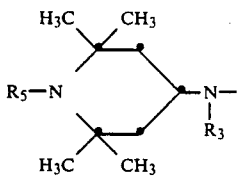

$R_2$ additionally is one of the groups

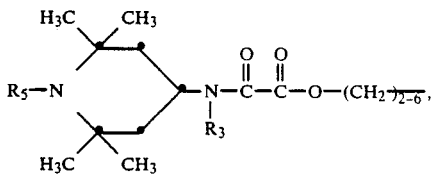

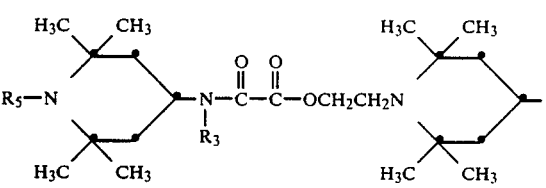

in which $R_3$ is as defined in this claim and $R_5$ is hydrogen or methyl.

4. Compounds of the formula

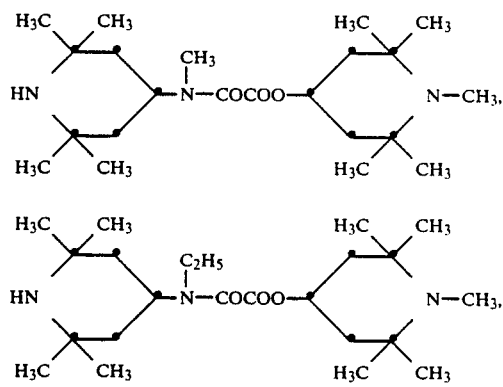

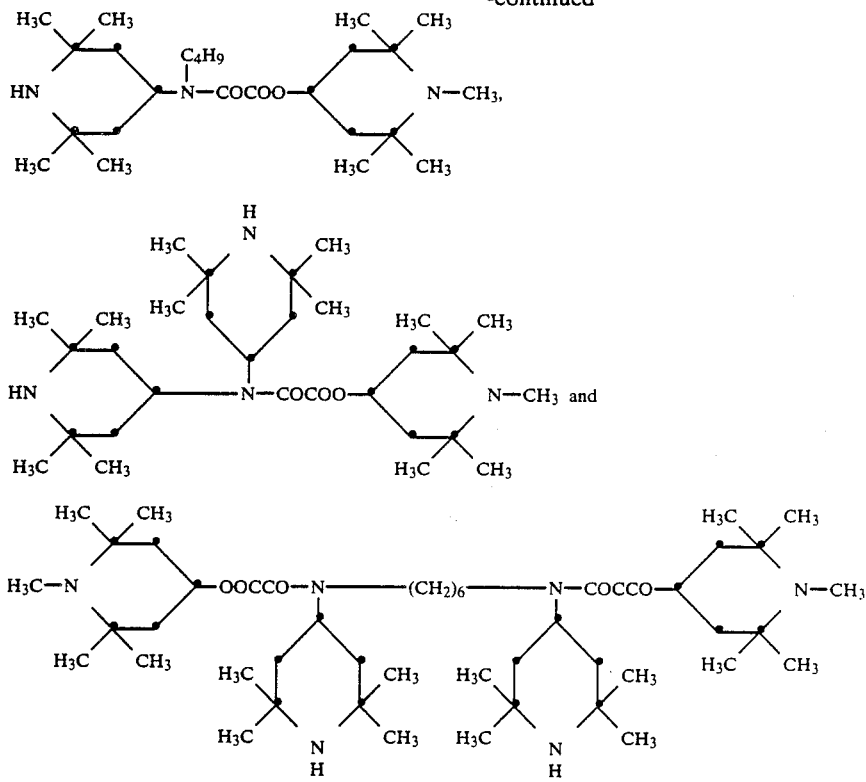
according to claim 1.
5. A compound of the formula (I) according to claim 1, in which m is 1.
6. A compound of the formula (I) according to claim 1, in which m is 2.